(12) United States Patent
Kirsch

(10) Patent No.: US 8,585,721 B2
(45) Date of Patent: Nov. 19, 2013

(54) MESH FIXATION SYSTEM

(75) Inventor: David S. Kirsch, Madison, CT (US)

(73) Assignee: Covidien LP, Mansfield, MA (US)

( * ) Notice: Subject to any disclaimer, the term of this patent is extended or adjusted under 35 U.S.C. 154(b) by 73 days.

(21) Appl. No.: 13/299,441

(22) Filed: Nov. 18, 2011

(65) Prior Publication Data

US 2013/0096584 A1 Apr. 18, 2013

Related U.S. Application Data

(60) Provisional application No. 61/546,269, filed on Oct. 12, 2011.

(51) Int. Cl.
*A61B 17/08* (2006.01)

(52) U.S. Cl.
USPC .......................................................... 606/151

(58) Field of Classification Search
USPC .................. 606/75, 139, 142–143, 151, 157, 606/219–221, 232, 250, 285; 623/23.72; 227/902; 24/710.5, 711.1, 704.1, 24/704.2; 206/338–347; 411/433, 444, 411/476, 457, 472, 456, 921
See application file for complete search history.

(56) References Cited

U.S. PATENT DOCUMENTS

| | | | | |
|---|---|---|---|---|
| 3,166,072 A | * | 1/1965 | Sullivan, Jr. | 606/153 |
| 3,357,296 A | | 12/1967 | Lefever | |
| 4,060,089 A | * | 11/1977 | Noiles | 606/220 |
| 4,548,202 A | * | 10/1985 | Duncan | 606/220 |
| 4,932,960 A | * | 6/1990 | Green et al. | 606/220 |
| 5,176,692 A | | 1/1993 | Wilk et al. | |
| 5,366,460 A | | 11/1994 | Eberbach | |
| 5,569,272 A | | 10/1996 | Reed et al. | |
| 5,984,949 A | | 11/1999 | Levin | |
| 6,168,362 B1 | * | 1/2001 | Tucker et al. | 411/442 |
| 6,214,020 B1 | * | 4/2001 | Mulhauser et al. | 606/151 |
| 6,485,503 B2 | | 11/2002 | Jacobs et al. | |
| 6,497,707 B1 | | 12/2002 | Bowman et al. | |
| 6,695,856 B2 | | 2/2004 | Kieturakis et al. | |
| 6,811,555 B1 | * | 11/2004 | Willis et al. | 606/153 |
| 6,991,643 B2 | * | 1/2006 | Saadat | 606/221 |
| 7,184,826 B2 | * | 2/2007 | Cormier et al. | 604/21 |
| 7,413,570 B2 | | 8/2008 | Zamierowski | |

(Continued)

FOREIGN PATENT DOCUMENTS

EP 0130037 A1 1/1985
EP 1806102 A1 7/2007

(Continued)

OTHER PUBLICATIONS

Extended European Search Report dated Jan. 18, 2013 from corresponding European Application No. 12188402.7 (9 pgs.).

*Primary Examiner* — Thomas McEvoy
*Assistant Examiner* — David Eastwood

(57) ABSTRACT

A mesh fixation system is disclosed including a plurality of elongate members and each elongate member includes a plurality of longitudinally extending support members. Each support member is connected to an adjacent support member by a plurality of connecting members and the elongate member defines at least one opening extending therethrough between adjacent support members and adjacent connecting members. The mesh fixation system further includes a plurality of legs extending from each support member. The plurality of legs is adapted for insertion through a mesh and into a body tissue to secure the mesh to the body tissue.

20 Claims, 7 Drawing Sheets

(56) References Cited

U.S. PATENT DOCUMENTS

| | | | |
|---|---|---|---|
| 7,824,433 B2 * | 11/2010 | Williams | 606/285 |
| 2002/0173807 A1 | 11/2002 | Jacobs | |
| 2003/0069602 A1 * | 4/2003 | Jacobs et al. | 606/215 |
| 2004/0073222 A1 * | 4/2004 | Koseki | 606/75 |
| 2004/0097980 A1 | 5/2004 | Ferree | |
| 2004/0153075 A1 * | 8/2004 | Roger | 606/72 |
| 2004/0220591 A1 | 11/2004 | Bonutti | |
| 2005/0256532 A1 | 11/2005 | Nayak et al. | |
| 2005/0273104 A1 * | 12/2005 | Oepen et al. | 606/69 |
| 2006/0036266 A1 | 2/2006 | Sulamanidze et al. | |
| 2006/0161160 A1 * | 7/2006 | Sander et al. | 606/72 |
| 2007/0156145 A1 * | 7/2007 | Demakas et al. | 606/69 |
| 2008/0065154 A1 | 3/2008 | Allard et al. | |
| 2008/0207989 A1 | 8/2008 | Kaleta et al. | |
| 2009/0254103 A1 | 10/2009 | Deutsch | |

FOREIGN PATENT DOCUMENTS

| | | |
|---|---|---|
| ES | 2199026 A1 | 2/2004 |
| ES | 2199026 B1 * | 6/2005 |
| WO | WO 2007/017872 A2 | 2/2007 |

* cited by examiner

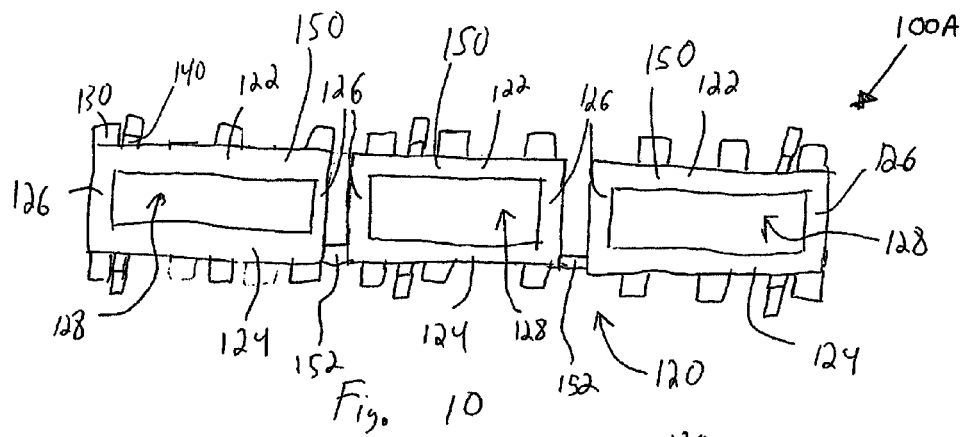
Fig. 10
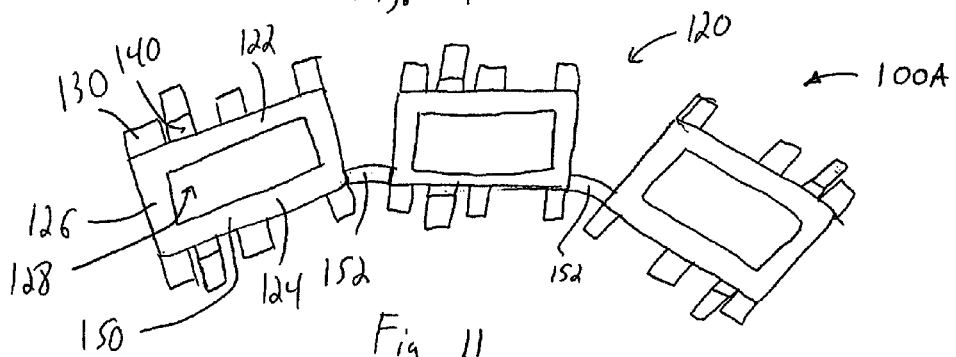
Fig. 11
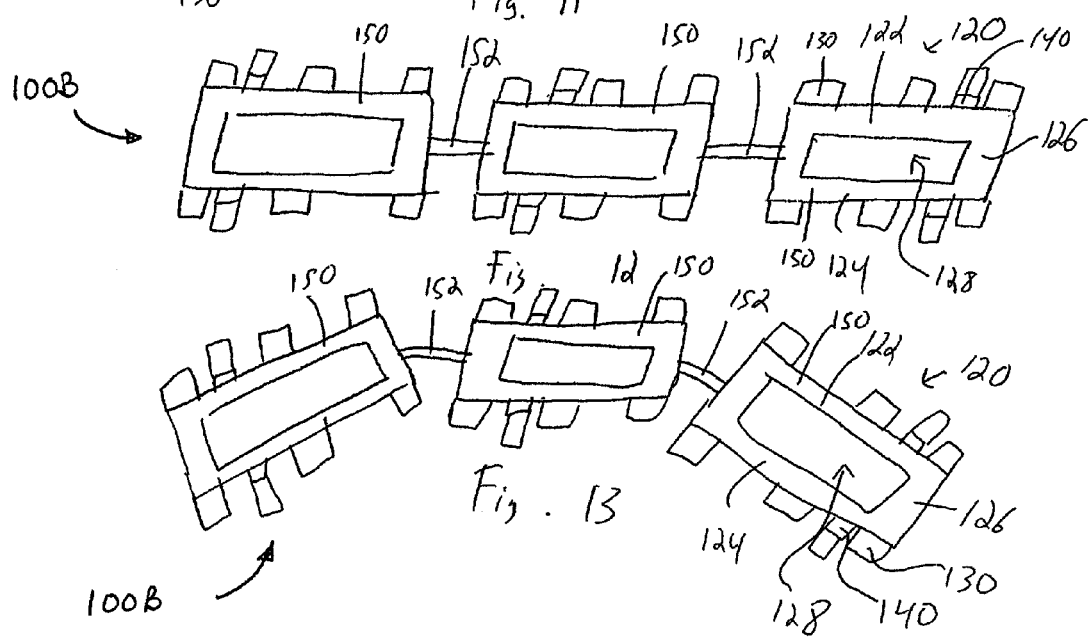
Fig. 12
Fig. 13

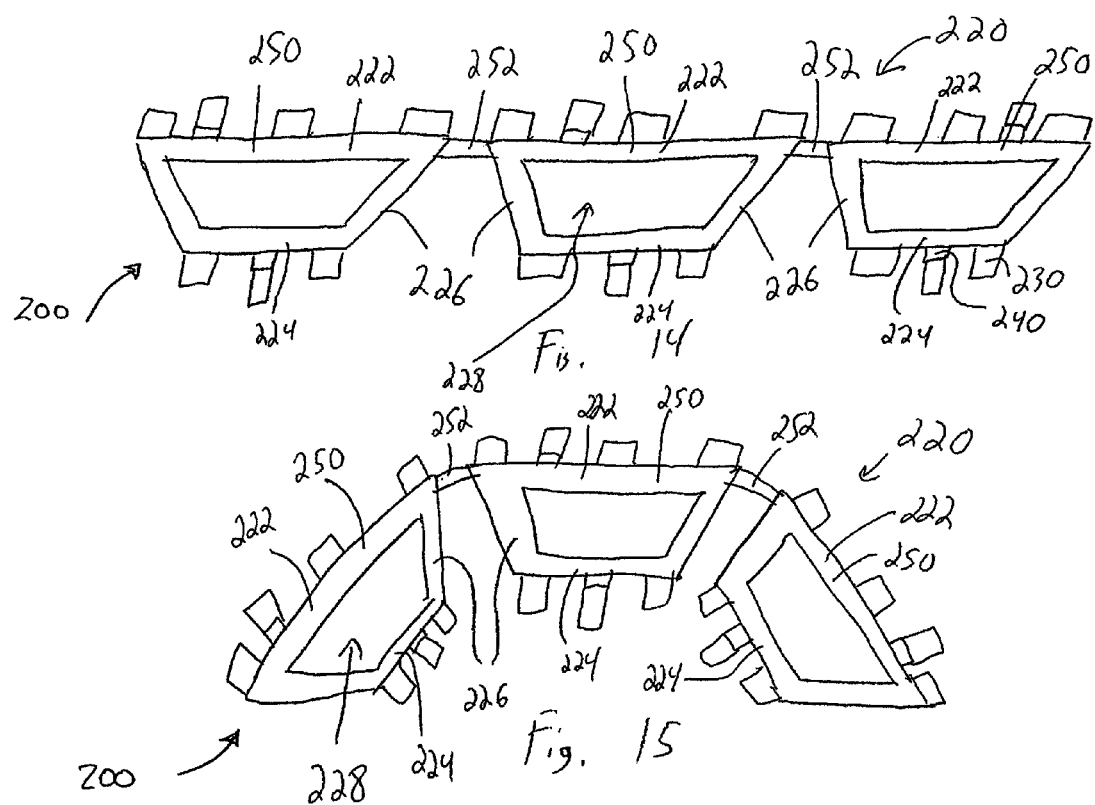

MESH FIXATION SYSTEM

CROSS-REFERENCE TO RELATED APPLICATIONS

The present application claims the benefit of and priority to U.S. Provisional Patent Application No. 61/546,269 filed on Oct. 12, 2011, the entirety of which being incorporated herein by reference.

BACKGROUND

1. Technical Field

The present disclosure relates generally to mesh fixation devices for securing objects to body tissue and, more particularly, to a mesh fixation system for securing a surgical mesh to underlying tissue during surgical procedures to repair body tissue, such as in hernia repair procedures.

2. Description of Related Art

In laparoscopic repair of hernias, surgical fasteners have been used to attach repair mesh over the hernia defect so that bowel and other abdominal tissue are blocked from forming an external bulge that is typical of abdominal hernias. The role of the fasteners is to keep the mesh in proper position until tissue ingrowth is adequate to hold the mesh in place under various internal and external conditions. Adequate ingrowth usually takes place in 6-8 weeks. After that time, the fasteners play no therapeutic role. Fixation anchors comprise a mesh fixation feature, or head, a mesh-tissue interface section, and a tissue-snaring feature that holds the anchor in place under force developed inside or outside the body.

An inguinal hernia is formed when small a loop of bowel or intestine protrudes through a weak place or defect within the lower abdominal muscle wall or groin. This condition is rather common, particularly in males. Hernias of this type can be a congenital defect or can be caused by straining or lifting heavy objects. The protrusion results in an unsightly bulge in the groin area often causing pain, reduced lifting ability, and in some cases, impaction of the bowel.

Surgery is a common solution to an inguinal hernia. The preferred surgical technique requires extracting the bowel from the defect, placing a surgical prosthesis such as a mesh patch over the open defect, and attaching the mesh patch to the inguinal floor with conventional sutures or with surgical fasteners or anchors. The repair is accomplished using either open or laparoscopic surgery. Surgical anchors are routinely used in the laparoscopic procedures owing to the difficulty in suturing under laparoscopic conditions.

SUMMARY

In the drawings, and in the following description, the term "proximal" should be understood as referring to the end of the pertinent structure that is closer to the clinician during proper use, while the term "distal" should be understood as referring to the end that is farther from the clinician, as is traditional and conventional in the art.

A mesh fixation system is disclosed including a plurality of elongate members and each elongate member includes a plurality of longitudinally extending support members. Each support member is connected to an adjacent support member by a plurality of connecting members and the elongate member defines at least one opening extending therethrough between adjacent support members and adjacent connecting members. The mesh fixation system further includes a plurality of legs extending from each support member. The plurality of legs is adapted for insertion through a mesh and into a body tissue to secure the mesh to the body tissue.

In another aspect, a mesh fixation system is disclosed including a mesh and a plurality of elongate members. Each elongate member includes a plurality of longitudinally extending support members each connected to an adjacent support member by a plurality of connecting members. Each elongate member defines at least one opening extending therethrough between adjacent support members and adjacent connecting members. The mesh fixation system further includes a plurality of legs extending from each support member. The plurality of legs is adapted for insertion through the mesh and into a body tissue to secure the mesh to the body tissue.

In any of the above aspects, each leg may include at least one fixation member adapted to limit withdrawal of the leg from the body tissue after insertion therein. The elongate members may be formed by injection molding. The elongate members may be formed of a polymer. The elongate members may be formed of a lactomer based system. The elongate members may be removably attached together. The support members may be disposed in substantially parallel alignment. The connecting members may be disposed in substantially parallel alignment. The connecting members may be disposed in transverse alignment to the support members. At least four elongate members may be included. Each support member may include at least four legs. The elongate members may be adapted to be separated before insertion into a body opening.

A method of affixing a mesh to body tissue over a hernia defect is disclosed including inserting the mesh through a body opening, positioning the mesh against the body tissue over the hernia defect, inserting a plurality of elongate members through the body opening, each elongate member including a plurality of legs, and driving the legs of each elongate member into the body tissue, at least one of the legs of each elongate member being driven through the mesh to secure the mesh to the body tissue.

In one aspect, each elongate member is initially attached to an adjacent elongate member and the method further includes separating the adjacent elongate members prior to insertion of the elongate members into the body opening.

In another aspect, at least one leg of each of the plurality of elongate members is driven through a different portion of the mesh adjacent the hernia defect.

In another aspect, each elongate member includes a first support member having a first plurality of legs and a second support member having a second plurality of legs where driving the legs of each elongate member into the body tissue includes driving at least one of the legs of the first support member through the mesh.

In another aspect, at least one leg of each of the first and second support members is driven through the mesh while the remaining legs of each of the first and second support members are driven only into the body tissue.

Although each aspect is described with reference to one of the systems and methods described above, it is contemplated that any of the above-mentioned aspects may be included with each of the above-mentioned systems or methods.

BRIEF DESCRIPTION OF THE DRAWINGS

The accompanying drawings, which are incorporated in and constitute a part of this specification, illustrate embodiments of the present disclosure and, together with a general description of the present disclosure given above, and the detailed description of the embodiments given below, serve to explain the principles of the present disclosure.

FIG. 10 is a top, plan view of an elongate member in accordance with an alternate embodiment of the present disclosure;

FIG. 11 is a top, plan view of the elongate member of FIG. 10, illustrating the elongate member in a flexed state;

FIG. 12 is a top, plan view of an elongate member in accordance with an alternate embodiment of the present disclosure;

FIG. 13 is a top, plan view of the elongate member of FIG. 12, illustrating the elongate member in a flexed state;

FIG. 14 is a top, plan view of an elongate member in accordance with an alternate embodiment of the present disclosure; and FIG. 15 is a top, plan view of the elongate member of FIG. 14, illustrating the elongate member in a flexed state.

DETAILED DESCRIPTION

Figure 1:
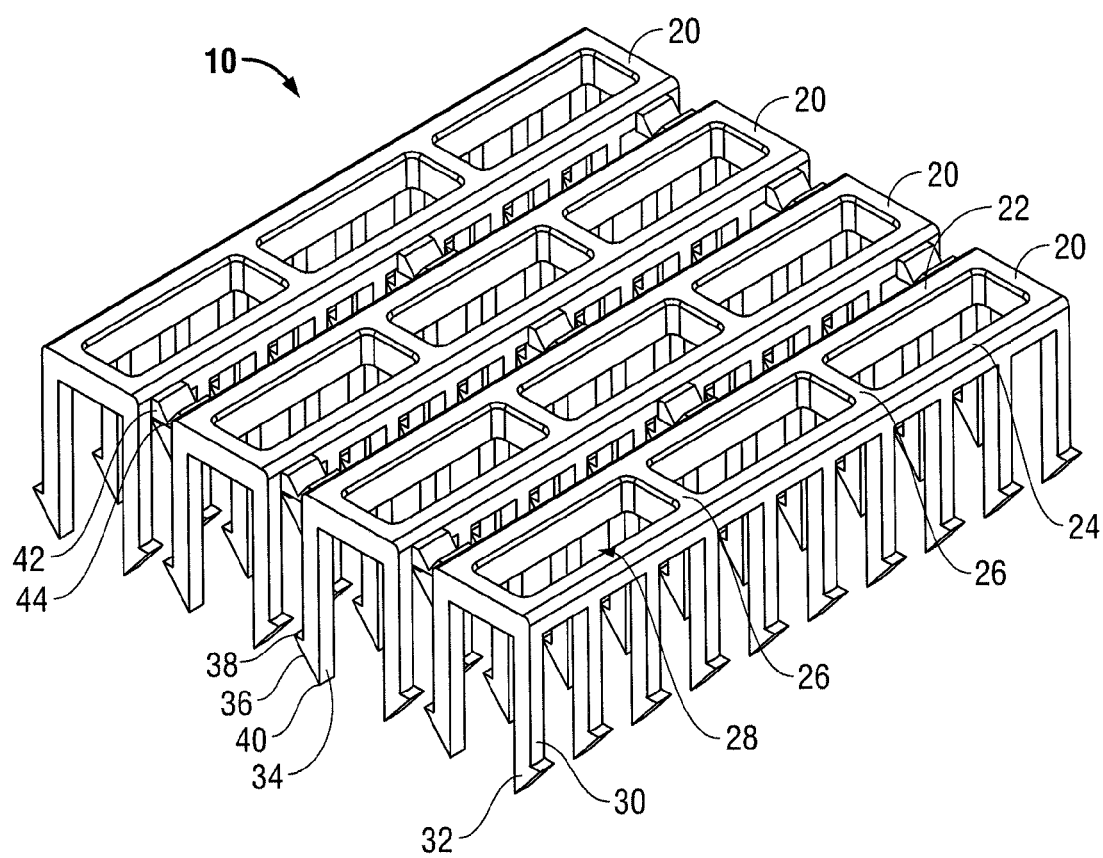
FIG. 1 is a perspective view illustrating a mesh fixation system in accordance with the present disclosure.

Various embodiments of the presently disclosed mesh fixation system, and methods of using the same, will now be described in detail with reference to the drawings wherein like references numerals identify similar or identical elements. In the drawings, and in the following description, the term "proximal" should be understood as referring to the end of the pertinent structure that is closer to the clinician during proper use, while the term "distal" should be understood as referring to the end that is farther from the clinician, as is traditional and conventional in the art.

Referring now in detail to the drawing figures, and in particular initially to FIG. 1, a mesh fixation device is generally shown as 10. Mesh fixation device 10 includes a plurality of elongate members 20 removably attached together.

As illustrated in FIGS. 2-5, each elongate member 20 includes a pair of longitudinally extending support members 22 and 24 respectively, and at least one connecting member 26 extending between the pair of support members 22, 24 to connect the pair of support members 22, 24 together. It is contemplated that each elongate member 20 may alternatively include only one support member or that each elongate member 20 may include three or more support members 22, 24 without departing from the scope of the present disclosure.

Figure 2:
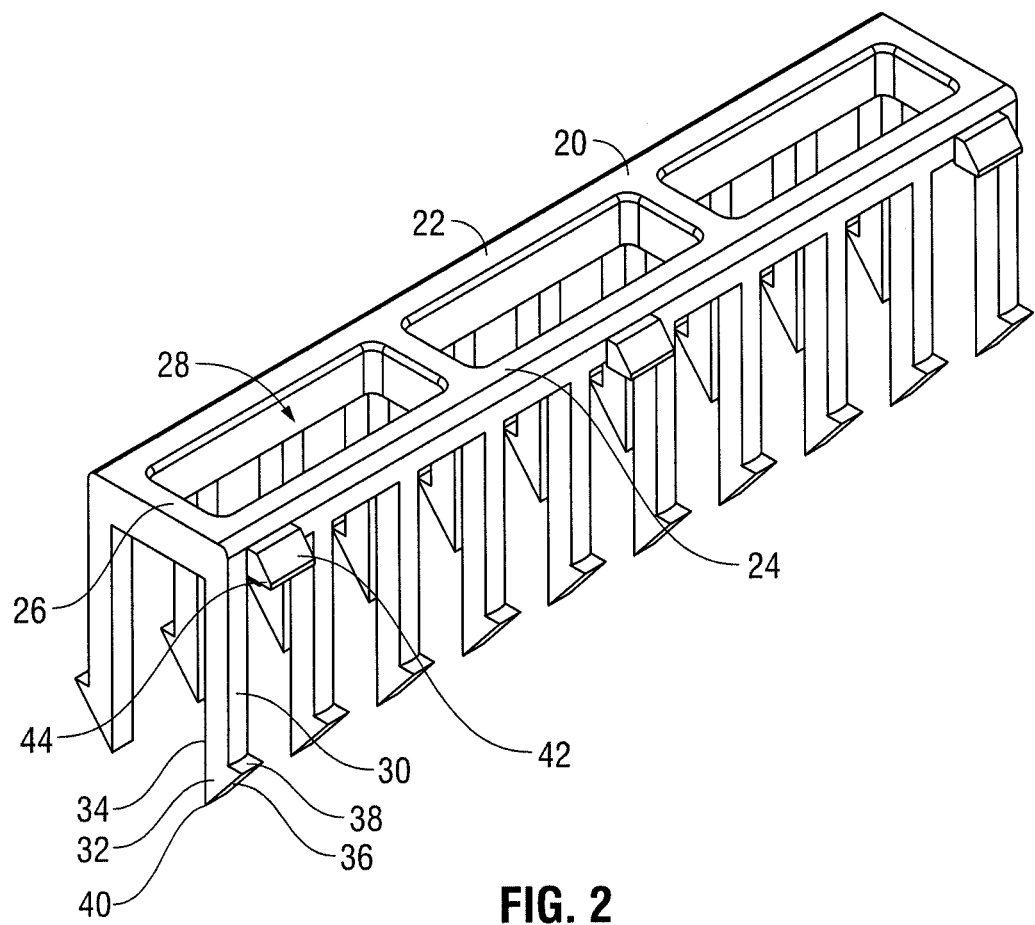
FIG. 2 is a perspective view illustrating an elongate member of the mesh fixation system of FIG. 1.
Figure 4:
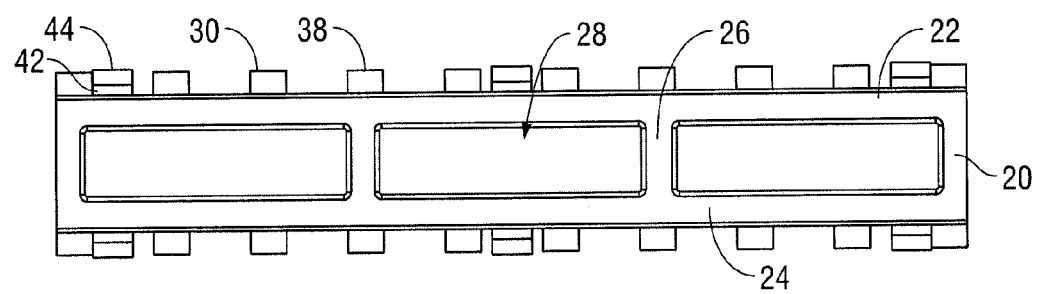
FIG. 4 is a top, plan view of the elongate member of FIG. 2.

As illustrated in FIGS. 2 and 4, the combination of support members 22, 24 and connecting members 26 of each elongate member 20 define a generally rectangular shape with the pair of support members 22, 24 disposed in substantially parallel alignment. However, it is contemplated within the scope of the present disclosure that support members 22, 24 and connecting members 26 may define other shapes such as, for example, a square shape, a triangular shape, a circular shape, an ovoid shape, a rhombic shape, a quadrilateral shape, another polygonal shape, or other suitable shapes for providing support to elongate member 20. It is also contemplated that support member 22 may be disposed at an angle relative to support member 24.

As illustrated in FIGS. 2 and 4, each connecting member 26 extends between support members 22 and 24 and is disposed substantially perpendicular relative to support member 22 and 24. It is contemplated however that connecting members 26 may alternatively be disposed at an angle to each of support members 22 and 24.

Each elongate member 20 includes at least one opening 28 extending therethrough defined by adjacent support members 22, 24 and adjacent connecting members 26. Opening 28 is adapted to facilitate tissue ingrowth and bio absorption of the elongate member 20. As illustrated in FIGS. 2 and 4, multiple openings 28 may be provided along the longitudinal length of each elongate member 20 to further assist in tissue ingrowth and bio absorption.

Figure 3:
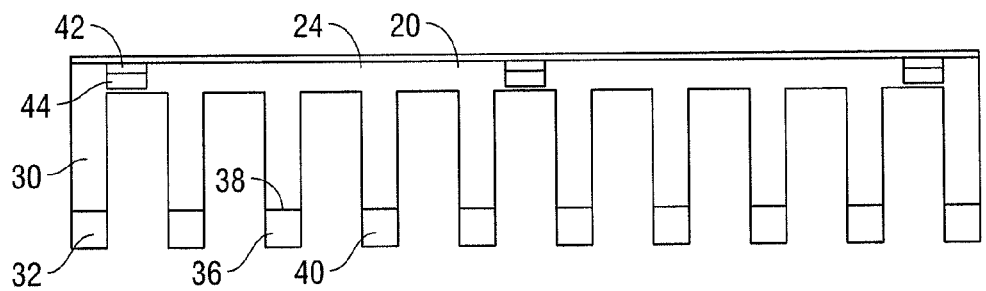
FIG. 3 is a side view of the elongate member of FIG. 2.

As illustrate in FIGS. 2-4, each support member 22, 24 includes a plurality of legs 30 extending therefrom. Legs 30 extend substantially perpendicular to support members 22 and 24 and define barbed tips 32. Each leg 30 is adapted for insertion through a mesh 100 and into tissue "T". Legs 30 may alternatively extend at an angle to support members 22 and 24. Although, as illustrated in FIGS. 3 and 4, legs 30 are spaced substantially uniformly along the length of each support member 22, 24, it is contemplated that legs 30 may be non-uniformly spaced where, for example, more legs per unit length may be found on a first of support members 22, 24 than that found on the second of support members 22, 24.

Figure 5:
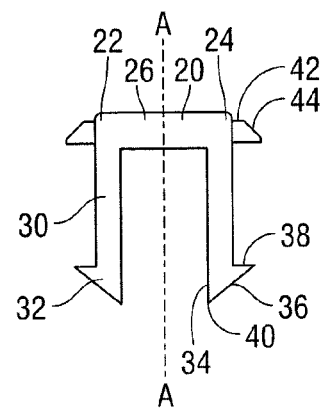
FIG. 5 is a front view of the elongate member of FIG. 2.

With reference to FIG. 5, barbed tips 32 of legs 30 are dimensioned to inhibit removal of legs 30 from tissue after legs 30 have been inserted therein. Each barbed tip 32 includes an inner portion 34 and an outer portion 36. Inner portion 34 extends substantially linearly from support members 22, 24 while outer portion 36 defines a flange 38 extending radially from the leg 30 and tapers towards the inner portion 34 from flange 38 to a tip 40. It is contemplated that inner portion 34 may be non-liner and may, for example, be curved or arcuate, and may also taper toward tip 40. Flanges 38 are adapted to inhibit removal of legs 30 from tissue once legs 30 have been inserted into tissue. As illustrated in FIG. 5, adjacent legs 30 of adjacent support members 22, 24 include flanges 38 which extend outward relative to an axis A-A and each other. This facilitates anchoring the elongate member 20 to the tissue since if elongate member 20 is pulled off axis at least one of flanges 38 will catch within the tissue to inhibit withdrawal. It is contemplated that flanges 38 may have other orientations, including, for example, extending inward towards axis A-A, e.g. from the inner member 34, or extending substantially parallel to the support member 22, 24 from which the leg 30 extends. Other types of barbed tips 32 may also be utilized including, for example, single barbs, compound barbs, V-lock barbs, bi-directional barbs, or other barbs suitable for inhibiting withdrawal or removal of legs 30 from tissue "T" after insertion therein. The barbs can be arranged in any suitable pattern about barbed tips 32 and legs 30 such as, for example, helical, spiral, linear, or randomly spaced. The pattern may be symmetrical or asymmetrical and more than one barb may be disposed on each of legs 30. Other methods of inhibiting withdrawal or removal of legs 30 from tissue "T" may also be included such as, for example, adhesives.

Figure 6:
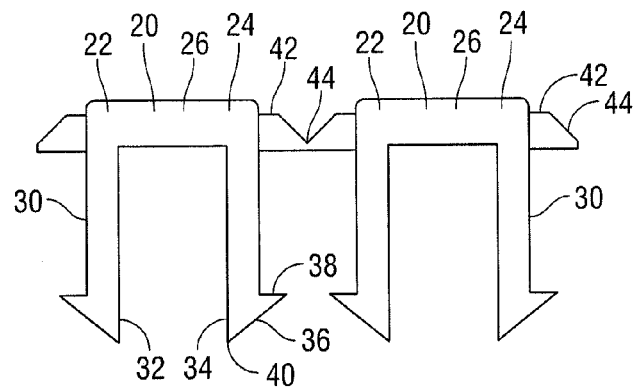
FIG. 6 is a front view of the mesh fixation system of FIG. 1, illustrating two of the elongate members attached together.

Referring now to FIGS. 1, 2, and 6, each elongate member 20 is attached to an adjacent elongate member 20 through an attachment joint 42. Attachment joints 42 are dimensioned and configured to break away or separate upon manipulation by a surgeon and may include, for example, perforations, scoring, or other suitable methods of weakening attachment joint 42 to allow for separation by the surgeon. For example, as illustrated in FIG. 6, attachment joint 42 may include a taper to an attenuated section 44 which defines a smaller cross section than the remaining sections of attachment joint 42. Attenuated section 44 allows the surgeon to manipulate mesh fixation device 10 with less force to detach one of elongate members 20 from an adjacent elongate member 20.

Mesh fixation device 10 may be formed through injection molding and may be formed of lactomer based systems or polymers such as, for example, lactides, glycolides, and others including trimethalyne carbonate (TMC, caprolactone, poly dioxanone). Each elongate member 20 is dimensioned and configured for insertion through a 5 mm port although larger or smaller sized elongate members 20 may be provided for insertion through openings which are larger or smaller than 5 mm.

During use, a surgeon initially finds or creates an opening in a patient's body through which surgical instruments may be inserted. The surgeon may insert a surgical access portal into the opening to facilitate the maintenance of an insufflated surgical space. Once the surgical site has been prepared a surgeon inserts a mesh 100 through the opening or access port and aligns the mesh 100 over a hernia defect "D" and surrounding tissue "T", as illustrated in FIG. 6. The surgeon then separates or detaches one of the elongate members 20 from the mesh fixation device 10 by twisting or snapping the attenuated sections 44 which attach the elongate member 20 to an adjacent elongate member 20. The surgeon inserts the separated elongate member 20 through the opening or port and positions the separated elongate member 20 over a portion of the mesh 100. The surgeon drives the legs 30 of the elongate member 20 through at least a portion of the mesh 100 such that the barbed tips 32 enter the tissue disposed beneath the mesh 100, thereby securing the mesh 100 to the tissue "T". The surgeon then repeats the process for each elongate member 20 until the mesh is secured to tissue "T" in place over the hernia defect "D".

Figure 7:
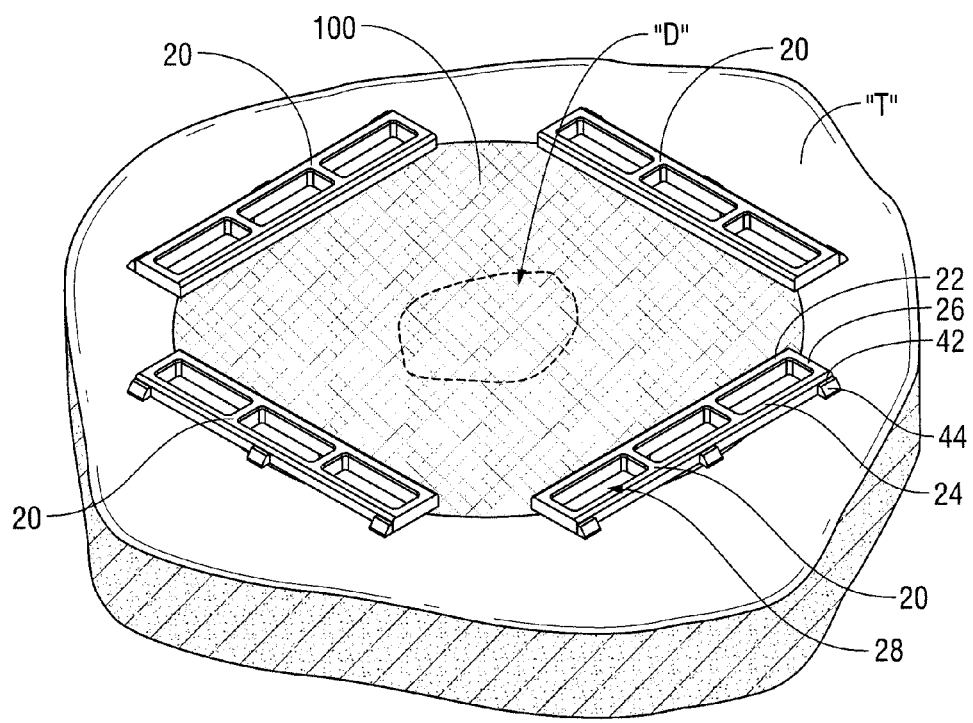
FIG. 7 is a perspective view of the mesh fixation system of FIG. 1, illustrating the mesh fixation system inserted through a mesh and into tissue to secure the mesh over a hernia defect.

Although only four elongate members 40 are illustrated in FIG. 7, it is contemplated that a larger number of elongate members 20 or a smaller number of elongate members 20 may be used for securing mesh 100. In addition, larger or smaller sized elongate members 20 may be provided for securing the mesh 100 to the tissue "T" where, for example, a smaller sized elongate member 20 may include fewer connecting members 26, openings, 28, and/or legs 30.

Figure 8:
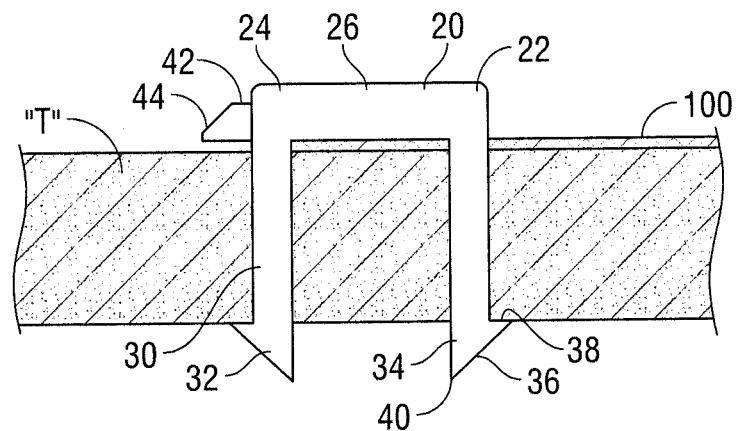
FIG. 8 is a front cross-sectional view of one of the elongate members of FIG. 7, illustrating the legs of the elongate member inserted through the mesh and into the body tissue.
Figure 9:
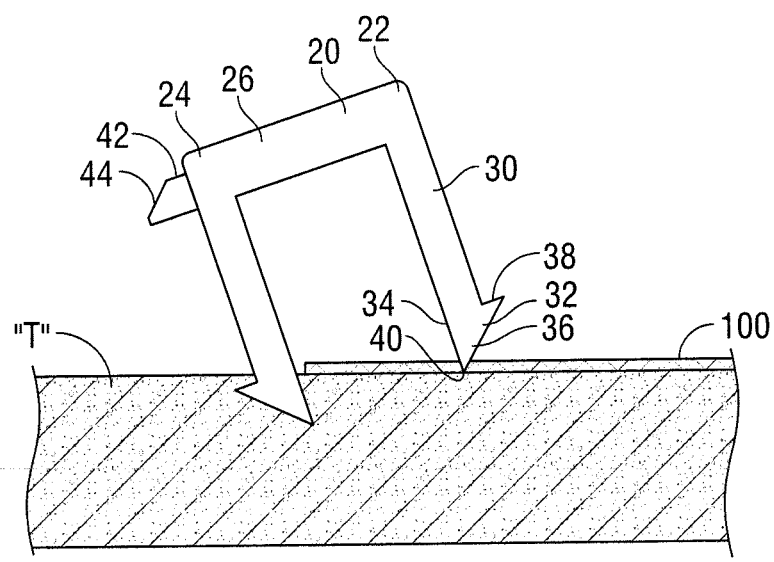
FIG. 9 is a front view of FIG. 8, illustrating the legs during insertion through the mesh and into the body tissue.

It is contemplated that only a portion of the legs 30 of elongate member 20 may be driven through the mesh 100 while the remaining portion of legs 30 are driven only through the tissue "T". For example, as illustrated in FIGS. 8 and 9, the legs 30 of support member 22 may be driven through the mesh 100 and tissue "T" while the legs 30 of support member 24 are driven only through the tissue "T". In another example, only a portion of the legs 30 of support member 22 are driven through the mesh 100 and tissue "T" while the remaining portion of legs 30 of support member 22 are driven through only tissue "T". In another example, only a portion of the legs 30 of each of support members 22 and 24 are inserted through the mesh 100 and tissue "T" while the remaining portion of legs 30 of each of support members 22 and 24 are inserted only through tissue "T". In another example, each leg 30 of support member 22 is inserted through the mesh 100 and tissue "T" while only a portion of the legs 30 of support member 24 are inserted through mesh 100 and tissue "T" with the remaining portion of legs 30 of support member 24 being inserted only through tissue "T".

As illustrated in FIG. 7, opposite elongate members 20 are aligned substantially parallel to one another when inserted through mesh 100 and tissue "T" and adjacent elongate members 20 are aligned substantially perpendicular to one another. It is contemplated the elongate members 20 may be aligned in other orientations with respect to adjacent and opposite elongate members 20 where, for example, opposite elongate members 20 may be angled with respect to one another and adjacent elongate members 20 may be oriented in a non-perpendicular fashion. Different orientations may be utilized, for example, if mesh 100 and/or hernia defect "D" is non-uniform in shape, if the location of the hernia defect "D" limits the positioning of the elongate members 20 and the mesh 100, or in other similar situations where the elongate members 20 may need to be positioned in other orientations.

Once mesh 100 is fixed in place by elongate members 20, the hernia defect "D" is covered and the surgery is complete. It is contemplated that elongate members 20 may be sufficiently resilient to bend or flex at least slightly where, for example, after surgery, movement of tissue "T" by the patient relative to the hernia defect "D" such as, for example, by breathing, stretching, or bending, may also flex or bend elongate members 20 without removing elongate members 20 from the mesh 100 or tissue "T".

With reference to FIGS. 10-15, in alternate embodiments which are similar to the above embodiment, elongate members 120 and 220 are disclosed wherein like references numerals identify similar or identical elements. In one embodiment, mesh fixation system 100A (FIGS. 10 and 11) includes elongate members 120 and bridge members 152. Alternatively, mesh fixation system 100B (FIGS. 12 and 13) includes elongate members 120 and bridge members 152. Further, mesh fixation system 200 includes elongate members 220 and bridge members 252. Elongate members 120 and 220 may include any or all of the features described above with regard to elongate member 20.

As illustrated in FIGS. 10-13, each elongate member 120 includes a plurality of sections 150 each having a pair of support members 122, 124 and a pair of connecting members 126. The support members 122, 124 and connecting members 126 of each section 150 define an opening 128 extending therethrough similar to openings 28 found in elongate members 20 above. As with elongate members 20 above, each section 150 includes a plurality of legs 130 extending from support members 122, 124. Each section 150 is connected to an adjacent section 150 by a bridge member 152. Bridge members 152 may be substantially aligned with support members 122, 124 of adjacent sections 150 (FIGS. 10 and 11), or may extend between connecting members 126 of adjacent sections 150 (FIGS. 12 and 13). Bridge members 152 allow adjacent sections 150 to move off axis or flex relative to one another during use. Bridge members 152 may be substantially more flexible than support members 122, 124. Each section 150 may also include an attachment joint 140 as described above with regard to elongate members 20.

During use, elongate member 120 may be flexed or bent at bridge members 152 to allow for positioning of elongate member 120 relative to mesh 100, where mesh 100 defines, for example, an arcuate or nonlinear edge, such that a greater number of legs 130 may be inserted through mesh 100 and into tissue "T" when elongate member 120 is flexed or bent than when elongate member 120 is not flexed or bent.

As illustrated in FIGS. 14 and 15, elongate member 220 is substantially similar to elongate member 120 except that the support members 222 of each section 250 are substantially longer than the support members 224 of each section 250. Bridge members 252 connect adjacent support members 222 together to allow sections 250 to flex or bend relative to adjacent sections 250. Because support members 224 of section 250 are shorter than support members 222, connecting members 226 of adjacent elongate members 220 are angled with respect to one another such that the distance between adjacent support members 222 is smaller than the distance between adjacent support members 224 when elongate member 220 is not flexed or bent. This longer distance between adjacent support members 224 allows adjacent sections 250 of elongate member 220 to flex or bend more than adjacent sections 150 of elongate member 120 before adjacent connecting members 126, 226 come into contact and limit further flexing or bending of bridge members 152, 252. Sections 150, 250 may still flex or bend further after contact between adjacent connecting members 126, 226 occurs.

Although the illustrative embodiments of the present disclosure have been described herein with reference to the accompanying drawings, the above description, disclosure, and figures should not be construed as limiting, but merely as exemplifications of particular embodiments. It is to be understood, therefore, that the disclosure is not limited to the precise embodiments described herein, and that various other changes and modifications may be effected by one skilled in the art without departing from the scope or spirit of the present disclosure.

What is claimed is:

1. A mesh fixation device comprising:
   a plurality of elongate members monolithically formed together, each elongate member comprising:
      a plurality of longitudinally extending support members, each support member connected to an adjacent support member by a plurality of connecting members, the elongate member defining at least one opening extending therethrough between adjacent support members and adjacent connecting members;
      an attachment joint coupling a first elongate member to a second elongate member, the first and second elongate members separable at the attachment joint upon the application of a force to the attachment joint; and
      a plurality of legs extending from each support member, the plurality of legs adapted for insertion through a mesh and into a body tissue to secure the mesh to the body tissue.

2. A mesh fixation device according to claim 1, wherein each of the legs includes at least one fixation member adapted to limit withdrawal of the leg from the body tissue after insertion therein.

3. A mesh fixation device according to claim 1, wherein the elongate members are formed by injection molding.

4. A mesh fixation device according to claim 1, wherein the elongate members are formed of a polymer.

5. A mesh fixation device according to claim 1, wherein the elongate members are formed of a lactomer based system.

6. A mesh fixation device according to claim 1, wherein the support members are disposed in substantially parallel alignment.

7. A mesh fixation device according to claim 1, wherein the connecting members are disposed in substantially parallel alignment.

8. A mesh fixation device according to claim 1, wherein the connecting members are disposed in transverse alignment to the support members.

9. A mesh fixation device according to claim 1, wherein each support member includes at least four legs.

10. A mesh fixation device according to claim 1, wherein the attachment joint includes a first portion attached to the first elongate member, a second portion attached to the second elongate member and an intermediate portion between the first portion and the second portion, the first and second elongate members separable at the intermediate portion upon the application of force to the attachment joint.

11. A mesh fixation device according to claim 10, wherein the intermediate portion defines a smaller cross-section than the first and second portions of the attachment joint.

12. A mesh fixation device according to claim 11, wherein the attachment joint defines a taper from the first and second portions to the intermediate portion.

13. A mesh fixation device according to claim 10, wherein the intermediate portion includes at least one of a perforation and scoring.

14. A mesh fixation device according to claim 10, wherein the first portion remains attached to the first elongate member and the second portion remains attached to the second elongate member when the elongate members separate at the intermediate portion.

15. A mesh fixation device according to claim 1, wherein each of the elongate members is configured for insertion through a 5 mm opening.

16. A mesh fixation system comprising:
   a mesh; and
   a plurality of elongate members monolithically formed together, each elongate member including:
      a plurality of longitudinally extending support members, each support member connected to an adjacent support member by a plurality of connecting members, the elongate member defining at least one opening extending therethrough between adjacent support members and adjacent connecting members;
      an attachment joint coupling a first elongate member to a second elongate member, the first and second elongate members separable at the attachment joint upon the application of a force to the attachment joint; and
      a plurality of legs extending from each support member, the plurality of legs adapted for insertion through the mesh and into a body tissue to secure the mesh to the body tissue.

17. A mesh fixation system according to claim 16, wherein four elongate members are included.

18. A mesh fixation system according to claim 16, wherein each leg includes at least one fixation member adapted to limit withdrawal of the leg from the body tissue after insertion therein.

19. A mesh fixation system according to claim 16, wherein the elongate members are removably attached together and adapted to be separated before insertion into a body opening.

20. A mesh fixation system according to claim 16, wherein each support member includes at least four legs.

* * * * *